US010814308B2

(12) United States Patent
Lee et al.

(10) Patent No.: US 10,814,308 B2
(45) Date of Patent: Oct. 27, 2020

(54) SUPERABSORBENT POLYMER COMPOSITION

(71) Applicant: LG Chem, Ltd., Seoul (KR)

(72) Inventors: Jin Woo Lee, Daejeon (KR); Young Sam Kim, Daejeon (KR); Jin Uk Choi, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 16/479,359

(22) PCT Filed: Oct. 19, 2018

(86) PCT No.: PCT/KR2018/012433
§ 371 (c)(1),
(2) Date: Jul. 19, 2019

(87) PCT Pub. No.: WO2019/103316
PCT Pub. Date: May 31, 2019

(65) Prior Publication Data
US 2019/0351391 A1    Nov. 21, 2019

(30) Foreign Application Priority Data

Nov. 27, 2017 (KR) ......................... 10-2017-0159735

(51) Int. Cl.
| | |
|---|---|
| *B01J 20/26* | (2006.01) |
| *A61L 15/18* | (2006.01) |
| *A61L 15/20* | (2006.01) |
| *A61L 15/24* | (2006.01) |
| *A61L 15/46* | (2006.01) |
| *A61L 15/60* | (2006.01) |
| *B01J 20/10* | (2006.01) |
| *B01J 20/22* | (2006.01) |
| *B01J 20/30* | (2006.01) |

(52) U.S. Cl.
CPC ............ *B01J 20/267* (2013.01); *A61L 15/18* (2013.01); *A61L 15/20* (2013.01); *A61L 15/24* (2013.01); *A61L 15/46* (2013.01); *A61L 15/60* (2013.01); *B01J 20/10* (2013.01); *B01J 20/22* (2013.01); *B01J 20/223* (2013.01); *B01J 20/3021* (2013.01); *B01J 20/3085* (2013.01); *A61L 2300/102* (2013.01); *A61L 2300/404* (2013.01)

(58) Field of Classification Search
CPC ......... B01J 20/26; B01J 20/267; B01J 20/10; B01J 20/22; B01J 20/223; B01J 20/3021; B01J 20/3085; A61L 5/20; A61L 15/24; A61L 15/46; A61L 15/60; A61L 2300/102; A61L 2300/404
USPC ...................................................... 502/402
See application file for complete search history.

(56) References Cited

U.S. PATENT DOCUMENTS

| | | |
|---|---|---|
| 4,990,338 A | 2/1991 | Blank et al. |
| 6,146,688 A | 11/2000 | Morgan et al. |
| 6,469,080 B2 | 10/2002 | Miyake et al. |
| 6,572,926 B1 | 6/2003 | Morgan et al. |
| 7,851,653 B2 | 12/2010 | Getman et al. |
| 7,858,141 B2 | 12/2010 | Getman et al. |
| 8,846,823 B2 | 9/2014 | Nakamura et al. |
| 2003/0135172 A1 | 7/2003 | Whitmore et al. |
| 2007/0060691 A1 | 3/2007 | Kim |
| 2009/0205116 A1 | 8/2009 | Stone et al. |
| 2010/0260645 A1 | 10/2010 | Low |
| 2010/0292078 A1 | 11/2010 | Braig et al. |
| 2012/0196953 A1 | 8/2012 | Ziolkowski et al. |
| 2014/0371352 A1 | 12/2014 | Dantin et al. |
| 2017/0073478 A1 | 3/2017 | Joo et al. |
| 2017/0216815 A1 | 8/2017 | Jang et al. |
| 2018/0228670 A1 | 8/2018 | Lee et al. |

FOREIGN PATENT DOCUMENTS

| | | |
|---|---|---|
| CN | 104159865 A | 11/2014 |
| CN | 106795319 A | 5/2017 |
| EP | 3056268 A1 | 8/2016 |
| EP | 3321313 A1 | 5/2018 |
| JP | H0359075 A | 3/1991 |
| JP | H10251530 A | 9/1998 |
| JP | 2005304763 A | 11/2005 |
| JP | 2013501742 A | 1/2013 |
| KR | 20080069661 A | 7/2008 |
| KR | 20100106425 A | 10/2010 |
| KR | 20120081113 A | 7/2012 |
| KR | 20160016714 A | 2/2016 |
| KR | 20160068768 A | 6/2016 |
| KR | 20170003491 A | 1/2017 |
| KR | 20170009546 A | 1/2017 |

(Continued)

OTHER PUBLICATIONS

International Search Report from Application No. PCT/KR2018/012433 dated Apr. 12, 2019, pp. 1-3.

(Continued)

Primary Examiner — Edward M Johnson
(74) Attorney, Agent, or Firm — Lerner, David, Littenberg, Krumholz & Mentlik, LLP

(57) ABSTRACT

A superabsorbent polymer composition includes superabsorbent polymer particles, having a crosslinked polymer of water-soluble ethylenically unsaturated monomers including acid groups, of which at least a part are neutralized; and a particulate antimicrobial agent having a quaternary ammonium salt of a silane-based compound. The superabsorbent polymer composition exhibits improved antimicrobial and deodorizing properties without deterioration of the superabsorbent polymer properties such as centrifugal retention capacity.

15 Claims, No Drawings

(56) References Cited

FOREIGN PATENT DOCUMENTS

| KR | 20170028852 A | 3/2017 |
|---|---|---|
| KR | 20170068384 A | 6/2017 |
| WO | 9746191 A1 | 12/1997 |
| WO | 9746194 A1 | 12/1997 |
| WO | 2014100777 A2 | 6/2014 |
| WO | 2017099422 A1 | 6/2017 |

OTHER PUBLICATIONS

Safety Data Sheet BIOSAFE HM 4100, Biosafe Quaternary Siloxane Powder, Date of Issue Mar. 26, 2014.
Technical Guide for Performance and Regulatory Compliance Biosafe, Retrieved Online Jan. 16, 2020, https://www.gelest.com/wp-content/uploads/Biosafe.pdf.
Third Party Observation for PCT/KR2018/012433 submitted Mar. 6, 2020, 11 pages.
Extended European Search Report including Written Opinion for Application No. EP18881922.1 dated Dec. 12, 2019.

SUPERABSORBENT POLYMER COMPOSITION

CROSS-REFERENCE TO RELATED APPLICATION(S)

The present application is a National Phase Entry under 35 U.S.C. § 371 of International Application No. PCT/KR2018/012433 filed on Oct. 19, 2018 which claims priority from Korean Patent Application No. 10-2017-0159735 filed on Nov. 27, 2017 all of which are herein incorporated by reference.

TECHNICAL FIELD

The present invention relates to a superabsorbent polymer composition, more specifically to a superabsorbent polymer composition that may exhibit improved antimicrobial and deodorizing properties without deterioration of basic absorption performance.

BACKGROUND

Super absorbent polymer (SAP) is synthetic polymer material that can absorb moisture of 500 to 1000 times of self-weight, and is also named differently as super absorbency material (SAM), absorbent gel material (AGM), etc. according to developing companies. The superabsorbent polymer began to be commercialized as sanitary items, and currently, it is being widely used as hygienic goods such as a disposable diaper and the like, water-holding material for soil, water stop material for civil engineering and architecture, sheets for raising seedling, freshness preservatives in the field of food circulation, fomentation material, and the like, or in the field of electric insulation.

Such superabsorbent polymer is most widely applied for hygienic goods or disposable absorption products such as child diapers or adult diapers. Among them, in case applied for adult diapers, secondary odor resulting from bacterial growth significantly gives consumers an unpleasant feeling. In order to solve this problem, there have been attempts to introduce various deodorizing or antimicrobial functional components into a superabsorbent polymer composition before.

However, in the existing attempts to introduce various deodorizing/antimicrobial functional components, the antimicrobial/deodorizing properties of superabsorbent polymer were not sufficient, and there were disadvantages in that the stability of superabsorbent polymer may be deteriorated and the basic absorption performance may be deteriorated, or the unit cost of a superabsorbent polymer composition may be increased too much due to the high costs of functional components.

Therefore, there is a continued demand for the development of a superabsorbent polymer composition that exhibits more improved antimicrobial and deodorizing properties without deterioration of basic absorption performance, and has excellent economical efficiency.

Technical Problem

The present invention provides a superabsorbent polymer composition that exhibits improved antimicrobial and deodorizing properties without deterioration of basic absorption performance, and hygienic goods comprising the same.

Technical Solution

The present invention provides a superabsorbent polymer composition comprising:

superabsorbent polymer particles comprising crosslinked polymer of water-soluble ethylenically unsaturated monomers including acid groups, of which at least a part are neutralized; and a particulate antimicrobial agent comprising a quaternary ammonium salt of a silane-based compound.

The present invention also provides hygienic goods comprising the superabsorbent polymer composition.

Effects of the Invention

According to the superabsorbent polymer composition, very improved antimicrobial property to bacteria inducing odor in hygienic goods such as an adult diaper, and the like, and the resultant deodorizing property can be exhibited without deterioration of basic absorption performance such as centrifugal retention capacity, absorbency under pressure, and the like. Particularly, such deodorizing/antimicrobial properties may be exhibited through the synergistic effect of raw materials having relatively low prices, thus contributing to the low unit cost and economic efficiency of the superabsorbent polymer composition.

DETAILED DESCRIPTION OF THE EMBODIMENTS

The terms used herein are only to explain specific embodiments, and are not intended to limit the present invention. A singular expression includes a plural expression thereof, unless it is expressly stated or obvious from the context that such is not intended. As used herein, the terms "comprise" or "include", etc. are intended to designate the existence of practiced characteristic, number, step, constructional element or combinations thereof, and they are not intended to preclude the possibility of existence or addition of one or more other characteristics, numbers, steps, constructional elements or combinations thereof.

Although various modifications can be made to the present invention and the present invention may have various forms, specific examples will be illustrated and explained in detail below. However, it should be understood that these are not intended to limit the present invention to specific disclosure, and that the present invention includes all the modifications, equivalents or replacements thereof without departing from the spirit and technical scope of the invention.

Hereinafter, a superabsorbent polymer composition according to specific embodiments of the present invention will be explained in more detail.

A superabsorbent polymer composition according to one embodiment of the invention comprises superabsorbent polymer particles comprising crosslinked polymer of water-soluble ethylenically unsaturated monomers including acid groups, of which at least a part are neutralized; and a particulate antimicrobial agent comprising a quaternary ammonium salt of a silane-based compound.

The superabsorbent polymer composition of one embodiment may exhibit improved deodorizing/antimicrobial properties than known before, by using a particulate antimicrobial agent in the form of a quaternary ammonium salt of a silane-based compound, which had not been applied for superabsorbent polymer before. Particularly, according to the result of experiments of the present inventors, such a component may preferably act on the superabsorbent polymer particles to very effectively remove bacteria acting as an offensive odor component in an adult diaper, and the like, and as the result, the superabsorbent polymer composition of one embodiment exhibits significantly improved deodorizing property.

And, these components do not inhibit the stability of the superabsorbent polymer composition, and thus, the superabsorbent polymer composition of one embodiment can maintain the basic absorption performance excellent, and the unit costs are relatively low, thus largely contributing to the low unit cost and economic efficiency of the superabsorbent polymer composition.

Therefore, the superabsorbent polymer composition of one embodiment can be very preferably applied for various hygienic goods such as an adult diaper, and the like.

Hereinafter, each component of the superabsorbent polymer composition of one embodiment will be explained in detail.

The superabsorbent polymer composition of one embodiment comprises a particulate antimicrobial agent comprising a quaternary ammonium salt of a silane-based compound, so as to achieve unique antimicrobial/deodorizing effects. And, the particulate antimicrobial agent may include a compound of the following Chemical Formula 1 as a main component:

Si(OH)₃-R1-N⁺(R2R3R4).X⁻  [Chemical Formula 1]

In the Chemical Formula 1, R1 is a C2-5 alkylene group; R2 to R4 are each independently, a C1-30 alkyl group, and at least one of them is a long chain alkyl group having a carbon number of 10 or more; and X is halogen.

More specifically, the particulate antimicrobial agent may have a structure of the following Chemical Formula 2, and the particulate antimicrobial agent comprising the Chemical Formula 2 as a main component is commercially available under the product name "Biosafe".

the stability or absorption property of superabsorbent polymer particles by such a component can be minimized.

Meanwhile, the superabsorbent polymer composition of one embodiment may further comprise a chelating agent including EDTA or an alkali metal salt thereof and/or a mixture of organic acid and silicate-based salt, so as to achieve additional antimicrobial/deodorizing properties.

Among them, as the chelating agent, those well known to a person having ordinary knowledge in the art, for example, a sodium salt of EDTA-2Na (EDTA-2Na) or amine acetic acid compounds may be used, and among them, a sodium salt of EDTA-2Na (EDTA-2Na) may be preferably used. In addition, amine acetic acid compounds selected from the group consisting of ethylene diamine tetraacetic acid, cyclohexane diamine tetraacetic acid, diethylene triamine pentaacetic acid, ethyleneglycol-bis-(aminoethylether)-N,N,N'-triacetic acid, N-(2-hydroxyethyl)-ethylene diamine-N,N,N'-triacetic acid, and triethylene tetraamine hexaacetic acid, or various chelating agents may be used.

Such a chelating agent may exist on the superabsorbent polymer particles to cause a synergistic effect with the particulate antimicrobial agent, or the mixture of organic acid and a silicate-based salt, and as the result, the superabsorbent polymer composition of one embodiment may exhibit improved deodorizing/antimicrobial properties.

The chelating agent may be included in the content of 0.1 to 3 parts by weight, or 0.5 to 2 parts by weight, based on 100 parts by weight of the superabsorbent polymer particles. Thereby, the antimicrobial/deodorizing properties of the superabsorbent polymer composition can be further improved, and simultaneously, the deterioration of the stability or absorption property of the superabsorbent polymer particles can be minimized.

Meanwhile, the superabsorbent polymer composition of one embodiment may further comprise a mixture of organic acid and a silicate-based salt. Such organic acid and silicate-based salt may also exist on the superabsorbent polymer particles.

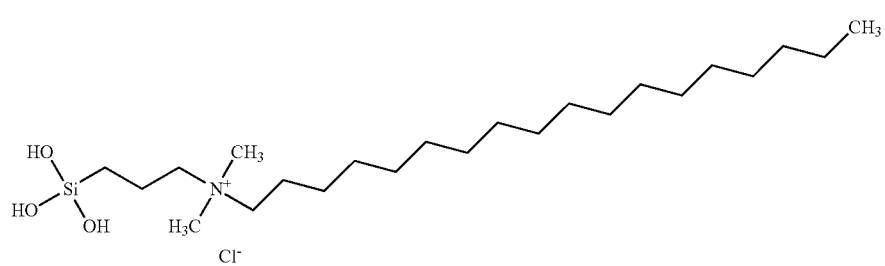

[Chemical Formula 2]

As the particulate antimicrobial agent, commercialized products may be acquired and used, or it may be directly synthesized by the methods known in U.S. Pat. Nos. 6,572,926, 6,146,688, 7,851,653 or 7,858,141.

Such a particulate antimicrobial agent may be added to superabsorbent polymer in the form of particles, and thereby, the superabsorbent polymer composition of one embodiment may exhibit more excellent deodorizing/antimicrobial properties.

Such a particulate antimicrobial agent may be included in the content of 0.2 to 5 parts by weight, or 0.5 to 4 parts by weight, based on 100 parts by weight of the superabsorbent polymer particles. Thereby, the antimicrobial/deodorizing properties of the superabsorbent polymer composition can be further improved, and simultaneously, the deterioration of Such a silicate-based salt may be in the form of a salt in which a silicate anion, and a cation of an alkali metal or an alkali earth metal are ionically bonded, and it may exist in the state of particles. Such silicate salt particles may include particles having a particle diameter of 150 μm or more and less than 600 μm in the content of about 80 to about 98 wt %, or about 90 to about 99 wt %, or about 92 to about 99.3 wt %.

And, the organic acid mixed with the silicate-based salt may exist on the superabsorbent polymer particles in the state of particles having a particle diameter of 600 μm or less, or 150 μm to 600 μm.

When the organic acid and silicate-based salt have the above-described particle characteristics and particle size distributions, they may be appropriately maintained on the superabsorbent polymer particles, and thus, can more selectively and effectively adsorb bacteria/offensive odor components to physically/chemically remove them. As the result, the superabsorbent polymer of one embodiment may exhibit more improved antimicrobial/deodorizing properties. Furthermore, due to the particle states, when mixed with superabsorbent polymer, anti-caking performance may be exhibited.

The organic acid may be included in the content of about 90 to 99.5 wt %, or about 95 to 99.3 wt %, or about 97 to 99.0 wt %, based on the total weight of the mixture of organic acid and a silicate-based salt. Thus, inside and/or on the surface of the superabsorbent polymer particles, a large number of acid sites may be generated. If such acid sites are included, various offensive odor components may be physically adsorbed, and the hydrogen cations (H+) of the acid sites may bond with offensive odor components to form ammonium salts, thereby more effectively removing offensive odor components.

The organic acid may include one or more selected from the group consisting of citric acid, fumaric acid, maleic acid and lactic acid, but it is not limited thereto.

Meanwhile, the mixture of organic acid and silicate-based salt may be mixed with superabsorbent polymer in which water-soluble ethylenically unsaturated monomers are polymerized, and applied for hygienic goods such as a diaper, and the like.

According to one embodiment of the invention, the mixture of organic acid and a silicate-based salt may be included in the content of about 0.5 to about 5 parts by weight, or about 0.8 to about 5 parts by weight, or about 1 to about 4 parts by weight, based on 100 parts by weight of the superabsorbent polymer. If the contents of these components are too small, deodorizing property obtained by the organic acid, and the like may not be sufficient, and if the contents are too large, the properties of superabsorbent polymer may be deteriorated.

The mixture of organic acid and a silicate-based salt may be prepared by a common method of mixing the organic acid and silicate-based salt. Although such a mixture may be prepared by previously mixing these two components, each component may be mixed with a particulate antimicrobial agent and a chelating agent, and the like, after preparing superabsorbent polymer particles, as described below.

Meanwhile, the kind or preparation method of the superabsorbent polymer that is mixed with the particulate antimicrobial agent, optionally, the chelating agent, and the mixture of organic acid and a silicate-based salt may be those commonly used in the art, and the steps and method of mixing these components with the superabsorbent polymer are not specifically limited.

For example, the superabsorbent polymer may be obtained by progressing thermal polymerization or photopolymerization of a monomer composition comprising water soluble ethylenically unsaturated monomers and a polymerization initiator to obtain hydrogel polymer, and drying, grinding, sieving it, and if necessary, surface crosslinking or fine powder reassembly process, and the like may be further conducted.

For reference, throughout the specification, "superabsorbent polymer" means to include crosslinked polymer in which water-soluble ethylenically unsaturated monomers including acid groups, of which at least a part are neutralized, are polymerized; base polymer made in the form of powder by drying and grinding the crosslinked polymer; or those made suitable for the productization by subjecting the crosslinked polymer or base polymer to additional processes, for example, surface crosslinking, fine powder reassembly, drying, grinding, sieving, and the like, according to the context.

As the water-soluble ethylenically unsaturated monomers, any monomers commonly used for the preparation of superabsorbent polymer may be used without specific limitations. As the water-soluble ethylenically unsaturated monomers, one or more monomers selected from the group consisting of anionic monomers and salts thereof, non-ionic hydrophilic group containing monomers and amino group containing unsaturated monomers and quaternarized products thereof may be used.

Specifically, one or more selected from the group consisting of anionic monomers and salts thereof such as (meth)acrylic acid, maleic anhydride, fumaric acid, crotonic acid, itaconic acid, 2-acryloylethane sulfonic acid, 2-methacryloylethane sulfonic acid, 2-(meth)acryloyl propane sulfonic acid, or 2-(meth)acrylamido-2-methyl propane sulfonic acid; non-ionic hydrophilic group containing monomers such as (meth)acrylamide, N-substituted (meth)acrylate, 2-hydroxyethyl (meth)acrylate, 2-hydroxypropyl (meth)acrylate, methoxy polyethylene glycol (meth)acrylate, or polyethylene glycol (meth)acrylate; and amino group containing unsaturated monomers such as (N,N)-dimethylaminoethyl (meth)acrylate, (N,N)-dimethylaminopropyl (meth)acrylamide, and quarternized products thereof, may be used.

More preferably, as the water soluble ethylenically unsaturated monomers, acrylic acid or salts thereof, for example, acrylic acid or an alkali metal salt such as a sodium salt thereof may be used, and in case such monomers are used, superabsorbent polymer having more excellent properties can be prepared. In case an alkali metal salt of acrylic acid is used as the water soluble ethylenically unsaturated monomers, acrylic acid may be neutralized with a basic compound such as caustic soda (NaOH) before use.

A polymerization initiator that is used when polymerizing the water-soluble ethylenically unsaturated monomers is not specifically limited as long as it is commonly used for the preparation of superabsorbent polymer.

Specifically, as the polymerization initiator, a thermal polymerization initiator or a photopolymerization initiator by UV irradiation may be used according to a polymerization method. However, even in the case of photopolymerization, since a certain amount of heat is generated by UV irradiation, etc., and heat is generated to some degree according to the progression of an exothermic polymerization reaction, a thermal polymerization initiator may be additionally included.

The photopolymerization initiator is not limited in terms of its construction, as long as it is a compound capable of forming a radical by light such as UV.

According to one embodiment of the invention, the monomer composition may further comprise an internal crosslinking agent as the raw material of superabsorbent polymer. As the internal crosslinking agent, a crosslinking agent having one or more functional groups capable of reacting with the water soluble substituents of the water soluble ethylenically unsaturated monomers, and having one or more ethylenically unsaturated groups; or a crosslinking agent having two or more functional groups capable of reacting with the water soluble substituents of the monomers and/or the water soluble substituents formed by the hydrolysis of the monomers may be used.

As specific examples of the internal crosslinking agent, C8-12 bisacrylamide, bismethaacrylamide, C2-10 polyol poly(meth)acrylate or C2-10 polyol poly(meth)allylether, and the like may be mentioned, and more specifically, one or more selected from the group consisting of N,N'-methylene bis(methacrylate), ethylene oxy(methacrylate), polyethylene oxy(methacrylate), propylene oxy(methacrylate), glycerin diacrylate, glycerin triacrylate, trimethylol triacrylate, triallyl amine, triaryl cyanurate, triallyl isocyanate, polyethylene glycol, diethylene glycol and propylene glycol may be used.

In the preparation method, the monomer composition may further comprise additives such as a thickener, a plasticizer, a preservation stabilizer, an antioxidant, etc., as necessary.

The above explained raw materials such as water soluble ethylenically unsaturated monomers, a photopolymerization initiator, a thermal polymerization initiator, an internal crosslinking agent, and additives may be prepared in the form of a solution dissolved in a solvent.

Meanwhile, a method of forming hydrogel polymer by the thermal polymerization or photopolymerization of the monomer composition is not specifically limited in terms of its construction, as long as it is a commonly used polymerization method.

Specifically, the polymerization method is largely classified into thermal polymerization and photopolymerization according to an energy source. Commonly, thermal polymerization may be progressed in a reactor equipped with a stirring axis such as a kneader, and, photopolymerization may be progressed in a reactor equipped with a movable conveyer belt, but the above explained polymerization methods are no more than examples, and the present invention is not limited thereto.

Here, the moisture content of hydrogel polymer obtained by such a method may be about 40 to about 80 wt %. Throughout the specification, the "moisture content" is the content of moisture occupied based on the total weight of hydrogel polymer, and it means a value obtained by subtracting the weight of polymer of a dry state from the weight of hydrogel polymer. Specifically, it is defined as a value calculated by measuring the weight loss according to moisture evaporation in the polymer while raising the temperature of polymer through infrared heating to dry. At this time, the drying condition is set up such that the temperature is raised from room temperature to about 180° C. and then maintained at 180° C., and the total drying time is 20 minutes including a temperature raising step of 5 minutes.

Next, the obtained hydrogel polymer is dried.

Wherein, a coarse grinding step may be further conducted before drying the hydrogel polymer so as to increase drying efficiency.

Here, grinders that can be used in the coarse grinding is not limited in terms of the constructions, but specifically, one selected from the group consisting of a vertical pulverizer, a turbo cutter, a turbo grinder, a rotary cutter mill, a cutter mill, a disc mill, a shred crusher, a crusher, a chopper, a disc cutter may be used, but the grinder is not limited thereto.

Through the coarse grinding step, the particle diameter of the hydrogel polymer may be controlled to about 2 to about 10 mm.

The hydrogel polymer coarsely ground as explained above, or hydrogel polymer immediately after polymerization that does not subjected to the coarse grinding step is dried.

And, the drying method is not limited in terms of the construction as long as it is commonly used as a drying process of hydrogel polymer. Specifically, the drying step may be progressed by hot wind supply, infrared ray irradiation, ultrahigh frequency wave irradiation, or UV irradiation, etc. The polymer dried by such a method may exhibit a moisture content of about 0.1 to about 10 wt %.

Next, the dried polymer obtained through the drying step is ground.

The particle diameter of the polymer powder obtained after the grinding step may be 150 μm to 850 μm. As a grinder for grinding to such a particle diameter, specifically, a pin mill, a hammer mill, a screw mill, a roll mill, a disc mill, or a jog mill, etc. may be used, but the grinder is not limited thereto.

And, in order to manage the properties of the superabsorbent polymer powders finally productized after the grinding step, the polymer powders obtained after grinding may be subjected to a separate process of sieving according to the particle diameter. Preferably, polymer having a particle diameter of about 150 to about 850 μm is sieved.

According to one embodiment of the invention, the ground or sieved polymer may be subjected to a step of surface crosslinking. Wherein, the surface crosslinking agent is not limited in terms of its construction as long as it can react with the functional group of the polymer. As examples of the surface crosslinking agent, polyhydric alcohol compounds, multivalent alkylene carbonate compounds, or multivalent epoxy compounds, and the like may be mentioned.

The superabsorbent polymer particles obtained by the above process, the above explained particulate antimicrobial agent, and optionally, the chelating agent, and the mixture of organic salt and a silicate-based salt may be uniformly mixed to obtain the superabsorbent polymer composition of one embodiment of the present invention.

Wherein, a method of mixing is not specifically limited, and for example, superabsorbent polymer particles, a particulate antimicrobial agent, and the like may be put into a reactor and mixed; or a solution comprising a particulate antimicrobial agent, and the like may be sprayed to superabsorbent polymer; or superabsorbent polymer, and a particulate antimicrobial agent, and the like may be continuously fed into a reactor such as a continuously operated mixer and mixed.

Meanwhile, in the superabsorbent polymer composition of one embodiment, the superabsorbent polymer particles may further comprise residual iron ions derived from a monomer composition comprising water soluble ethylenically unsaturated monomers and/or an initiator, in the content of 3 ppmw or less, or 0.1 to 3 ppmw, based on the total monomers, and in this case, it may comprise the above explained chelating agent together.

In the preparation process of superabsorbent polymer particles, a polymerization initiator such as a common redox initiator, and the like may be used, and iron ions derived from the initiator may remain in the monomers and/or superabsorbent polymer particles. However, such iron ions may cause property deterioration of a superabsorbent polymer composition, but since the composition of one embodiment comprises a chelating agent, the residual amount of the iron ions may be reduced. As the result, the superabsorbent polymer composition of one embodiment may exhibit more excellent properties.

The superabsorbent polymer composition of one embodiment obtained as explained above may exhibit excellent antimicrobial/deodorizing effects and basic absorption properties.

Hereinafter, the actions and the effects of the invention will be explained in more detail, through specific examples of the invention. However, these examples are presented only as the illustrations of the invention, and the scope of the right of the invention is not limited thereby.

EXAMPLE

Example: Preparation of a Superabsorbent Polymer Composition

Example 1

100 parts by weight of acrylic acid monomers were mixed with 38.9 parts by weight of caustic soda (NaOH) and 103.9 parts by weight of water, and to the mixture, 0.1 parts by weight of a thermal polymerization initiator of sodium persulfate, 0.01 parts by weight of a photopolymerization initiator of diphenyl(2,4,6-trimethylbenzoyl)phosphine oxide, and 0.3 parts by weight of a crosslinking agent of polyethylene glycol diacrylate were added to prepare a monomer composition.

While the monomer composition was flowed at the flow rate of 243 kg/hr on the polymerization belt of a continuous belt polymerization reactor, of which internal temperature is maintained at 80° C., and on top of which a UV irradiation device having an intensity of 10 mW with a mercury UV lamp light source is installed, UV was irradiated for 1 minute, and a polymerization reaction was progressed for additional 2 minutes without a light source.

A gel type polymerization sheet emerging after the polymerization was finished was primarily cut using a Shredder type cutter, and then, coarsely ground through a meat chopper. Thereafter, it was dried at 180° C. for 30 minutes through a hot air dryer, and then, ground using a rotary mixer and sieved to 180 μm to 850 μm, thus preparing base polymer.

Into the base polymer, 0.1 wt % of ethylene glycol diglycidyl epoxide were introduced and uniformly mixed, and then, a surface treatment was progressed at 140° C. for 1 hour to obtain superabsorbent polymer.

Based on 100 parts by weight of the superabsorbent polymer, 2 parts by weight of a particulate antimicrobial agent comprising a quaternary ammonium salt of a silane-based compound (product name: Biosafe (including Chemical Formula 2)) were put in, and stirred at 500 rpm for 2 minutes using a Ploughshare blender. The prepared superabsorbent polymer composition was designated as Example 1.

Example 2

Superabsorbent polymer was prepared by the same method as Example 1.

Based on 100 parts by weight of the superabsorbent polymer, 2 parts by weight of a particulate antimicrobial agent comprising a quaternary ammonium salt of a silane-based compound (product name: Biosafe (including Chemical Formula 2)), and 2.02 parts by weight of a mixture including 99 wt % of citric acid and 1 wt % of sodium metasilicate salt were put in, and stirred at 500 rpm for 2 minutes using a Ploughshare blender. The prepared superabsorbent polymer composition was designated as Example 2.

Example 3

Superabsorbent polymer was prepared by the same method as Example 1.

Based on 100 parts by weight of the superabsorbent polymer, 2 parts by weight of a particulate antimicrobial agent comprising a quaternary ammonium salt of a silane-based compound (product name: Biosafe (including Chemical Formula 2)), and 1 part by weight of a sodium salt of EDTA (EDTA-2Na), were put in, and stirred at 500 rpm for 2 minutes using a Ploughshare blender. The prepared superabsorbent polymer composition was designated as Example 3.

Example 4

Superabsorbent polymer was prepared by the same method as Example 1.

Based on 100 parts by weight of the superabsorbent polymer, 2 parts by weight of a particulate antimicrobial agent comprising a quaternary ammonium salt of a silane-based compound (product name: Biosafe (including Chemical Formula 2)), 2.02 parts by weight of a mixture including 99 wt % of citric acid and 1 wt % of sodium metasilicate salt, and 1 part by weight of a sodium salt of EDTA (EDTA-2Na) were put in, and stirred at 500 rpm for 2 minutes using a Ploughshare blender. The prepared superabsorbent polymer composition was designated as Example 4.

Comparative Example 1

Superabsorbent polymer was prepared by the same method as Example 1. The prepared superabsorbent polymer itself was designated as Comparative Example 1.

Evaluation of the Properties of Superabsorbent Polymer

The properties of the superabsorbent polymer compositions of Examples 1 to 4 and Comparative Example 1 were measured as follows, and the results were shown in Table 1.

(1) Antimicrobial/Deodorizing Performance Test 50 ml of artificial urine inoculated with 390,000 CFU/ml of *Proteus mirabillis* (ATCC 29906) was incubated in an oven of 35° C. for 12 hours. The artificial urine and the artificial urine after incubated for 12 hours were designated as controls, and they were properly washed with 150 ml of a saline solution to measure CFU (Colony Forming Unit), thereby calculating the properties of controls.

Each 2 g of the superabsorbent polymer compositions of Examples and Comparative Examples were added to 50 ml of the artificial urine inoculated with 390,000 CFU/ml of *Proteus mirabillis* (ATCC 29906), and then, incubated in an oven of 35° C. for 12 hours. The artificial urine after incubated for 12 hours was properly washed with 150 ml of a saline solution to measure CFU (Colony Forming Unit). Thereby, the antimicrobial/deodorizing properties of each Example and Comparative Example were calculated/evaluated.

(2) CRC (Centrifugal Retention Capacity)

Centrifugal retention capacity (CRC) was measured according to EDANA method WSP 241.3. 0.2 g of the prepared superabsorbent polymer composition were put into a tea bag, and soaked in a 0.9% saline solution for 30 minutes. Thereafter, it was drained by gravity of 250 G for 3 minutes, and then, the amount of absorbed saline solution was measured.

TABLE 1

| | Additives | Incubation time (hr) | CFU/ml | LOG [CFU/ml] | CRC (g/g) |
|---|---|---|---|---|---|
| Control | Superabsorbent polymer not added | 0 | 390000 | 5.6 | |
| | | 12 | 130000000 | 8.1 | |
| Example 1 | Superabsorbent polymer + Biosafe(2 parts by weight) | 12 | 9400000 | 7.0 | 35.8 |
| Example 2 | Superabsorbent polymer + Biosafe(2 parts by weight) + Citric acid + silicate salt(2.02 parts by weight) | 12 | 6600000 | 6.8 | 35.9 |
| Example 3 | Superabsorbent polymer + Biosafe(2 parts by weight) + Chelating agent (1 part by weight) | 12 | 720000 | 5.9 | 35.5 |
| Example 4 | Superabsorbent polymer + Biosafe(2 parts by weight) + Chelating agent(1 part by weight) + Citric acid + silicate salt(2.02 parts by weight) | 12 | 1700000 | 6.2 | 35.3 |
| Comparative Example 1 | Superabsorbent polymer | 12 | 18000000 | 7.3 | 37.9 |

Referring to Table 1, it was confirmed that the superabsorbent polymer compositions of Examples, despite the addition of the functional additives, maintain centrifugal retention capacities equivalent to or more excellent than those of Comparative Examples, and simultaneously, exhibit improved antimicrobial/deodorizing properties.

The invention claimed is:

1. A superabsorbent polymer composition comprising superabsorbent polymer particles comprising a cross-linked polymer of water-soluble ethylenically unsaturated monomers including acid groups, of which at least a part are neutralized; and
a particulate antimicrobial agent comprising a quaternary ammonium salt of a silane-based compound.

2. The superabsorbent polymer composition according to claim 1, wherein the particulate antimicrobial agent includes a compound of the following Chemical Formula 1:

Si(OH)$_3$-R1-N$^+$(R2R3R4).X$^-$   [Chemical Formula 1]

wherein,
R1 is a C2-5 alkylene group;
R2 to R4 are each independently, a C1-30 alkyl group, and at least one of R2 to R4 is a long chain alkyl group having a carbon number of 10 or more; and
X is halogen.

3. The superabsorbent polymer composition according to claim 1, wherein the particulate antimicrobial agent is included in a content of 0.2 to 5 parts by weight, based on 100 parts by weight of the superabsorbent polymer particles.

4. The superabsorbent polymer composition according to claim 1, further comprising a chelating agent; or a mixture of an organic acid and a silicate-based salt.

5. The superabsorbent polymer composition according to claim 4, wherein the chelating agent comprises a sodium salt of EDTA(EDTA-2Na), ethylene diamine tetraacetic acid, cyclohexane diamine tetraacetic acid, diethylene triamine pentaacetic acid, ethyleneglycol-bis-(aminoethylether)-N,N,N'-triacetic acid, N-(2-hydroxyethyl)-ethylenediamine-N,N,N'-triacetic acid, or triethylene tetraamine hexaacetic acid.

6. The superabsorbent polymer composition according to claim 4, wherein the chelating agent is included in a content of 0.1 to 3 parts by weight, based on 100 parts by weight of the superabsorbent polymer particles.

7. The superabsorbent polymer composition according to claim 4, wherein the organic acid comprises citric acid, fumaric acid, maleic acid or lactic acid.

8. The superabsorbent polymer composition according to claim 4, wherein the silicate-based salt includes a salt in which a silicate anion, and a cation of alkali metal or alkali earth metal are bonded.

9. The superabsorbent polymer composition according to claim 4, wherein the organic acid is included in a content of 90 to 99.5 wt %, based on a total weight of the mixture of organic acid and silicate-based salt.

10. The superabsorbent polymer composition according to claim 4, wherein the mixture of organic acid and silicate-based salt is included in a content of 0.5 to 5 parts by weight, based on 100 parts by weight of the superabsorbent polymer particles.

11. The superabsorbent polymer composition according to claim 4, wherein the superabsorbent polymer composition further comprises a chelating agent including EDTA or an alkali metal salt thereof, and
the superabsorbent polymer particles further comprise residual iron ions derived from a monomer composition comprising water soluble ethylenically unsaturated monomers and an initiator, in a content of 3 ppmw or less.

12. A hygienic good comprising the superabsorbent polymer composition of claim 1.

13. The superabsorbent polymer composition according to claim 11, wherein the residual iron ions are in the content of 0.1 to 3 ppmw.

14. The superabsorbent polymer composition according to claim 8, wherein the silicate-based salt is sodium metasilicate salt.

15. The superabsorbent polymer composition according to claim 4, wherein the silicate -based salt is in a form of silicate salt particles wherein 80 to 98 wt % of the silicate salt particles have a particle diameter from 150 μm to 600 μm.

* * * * *